United States Patent [19]
Kuo et al.

[11] Patent Number: 4,848,900
[45] Date of Patent: Jul. 18, 1989

[54] COMPUTERIZED AUTOMATIC MONITORING AND RECORDING SYSTEM OF ERYTHROCYTE SEDIMENTATION PROCESS

[76] Inventors: Cheng-Deng Kuo; Jing-Jang Bai; I-Te Chang, all of 3 Fl., No. 89, Sec. 2, Keelung Rd., Taipei, Taiwan

[21] Appl. No.: 64,863

[22] Filed: Jun. 22, 1987

[51] Int. Cl.$^4$ ............................................. G01N 15/05
[52] U.S. Cl. ...................................... 356/39; 73/61.4
[58] Field of Search .................... 356/39; 346/33 ME; 73/61.4

[56] References Cited

U.S. PATENT DOCUMENTS

| | | | |
|---|---|---|---|
| 2,104,525 | 1/1938 | Proskouriakoff | 93/61.4 X |
| 2,982,170 | 5/1961 | Wyss | 356/39 X |
| 3,715,761 | 2/1973 | Drekter et al. | 356/39 X |
| 4,041,502 | 8/1977 | Williams et al. | 356/39 X |
| 4,118,974 | 10/1978 | Nozaki et al. | 356/39 X |

FOREIGN PATENT DOCUMENTS

| | | | |
|---|---|---|---|
| 2727400 | 12/1978 | Fed. Rep. of Germany | 73/61.4 |
| 2561776 | 9/1985 | France | 73/61.4 |

Primary Examiner—Vincent P. McGraw
Attorney, Agent, or Firm—Link & Leading

[57] ABSTRACT

An automatic monitoring and recording device for erythrocyte sedimentation employs a light source and a photodetector to detect the changes of light transmittance at the junction of plasma and red blood cell column. Changes of light transmittance at the junction reflect the descent of red blood cell column. The light source and photodetector pair is arranged so that it will track to the plasma - red blood cell column junction all the way the red blood cells fall. The whole course of erythroctye sedimentation is monitored and recorded automatically by a microcomputer.

5 Claims, 11 Drawing Sheets

MAIN PROGRAM

COMPUTERIZED AUTOMATIC MONITORING AND RECORDING SYSTEM OF ERYTHROCYTE SEDIMENTATION PROCESS

BACKGROUND OF THE INVENTION

The erythrocyte sedimentation rate (ESR) is a laboratory test that measures the distance, in millimeters, that erythrocytes fall in anticoagulated blood in one hour. It was introduced by Fahraeus in 1918, and has become one of the routine blood examinations in many hospital laboratories since then. The red blood cells (RBCs) are known to possess a net negative charge, the zeta potential, which slows down the sedimentation of RBCs when they are suspended in normal plasma. Alterations in the composition of plasma will reduce the zeta potential and induce aggregation and rouleaux formation of the RBCs, and their rate of sedimentation will then be increased. Plasma composition changes follow many tissue damage, inflammation and other pathological processes. Measuring ESR can, therefore, provide clinicians with information about underlying diseases. Three types of information can be obtained by means of ESR test: (I) to determine the presence or absence of disease; (II) to monitor the progression of an already recognized disease; (III) to measure the response to therapy. For instance, congestive heart failure, polycythemia and use of anti-inflammatory agents etc., are known to cause low ESR, whereas various types of infection, malignancy, collagen vascular diseases, and a variety of medications such as heparin, oral contraceptives etc., can cause elevated ESR. Of particular importance is the predictive value of markedly elevated ESR, values greater than 100 mm per hour. It is noted that a patient found to have a markedly elevated ESR has a 95 percent likelihood of an infectious, inflammatory, collagen vascular or neoplastic process. Further investigation is warranted for such patients. ESR is, therefore, useful as a "sickness index", or a "broad spectrum indicator" of disease.

Figure 1:
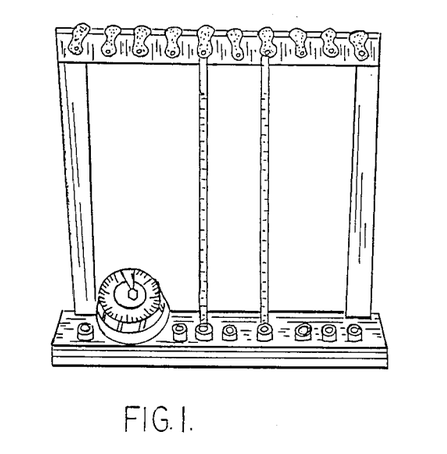
FIG. 1 is a photograph illustrating the operation of Westergren method that is still in use nowadays. A clock is employed to remind a technician of recording the ESR data at one hour after the start of the test.
Figure 2:
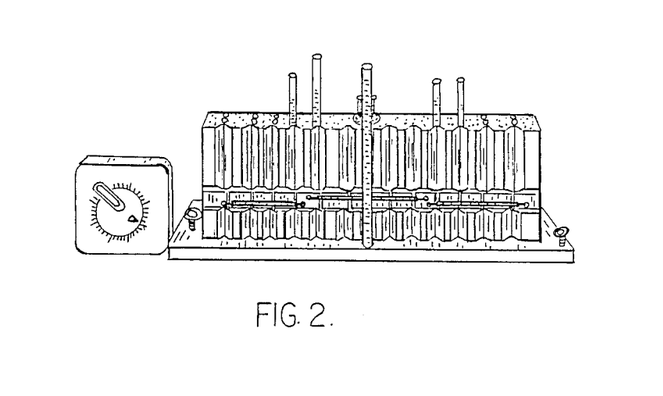
FIG. 2 is a photograph illustrating the operation of the Wintrobe-Landsberg method that is still in use nowadays. A clock is also used.
Figure 3:
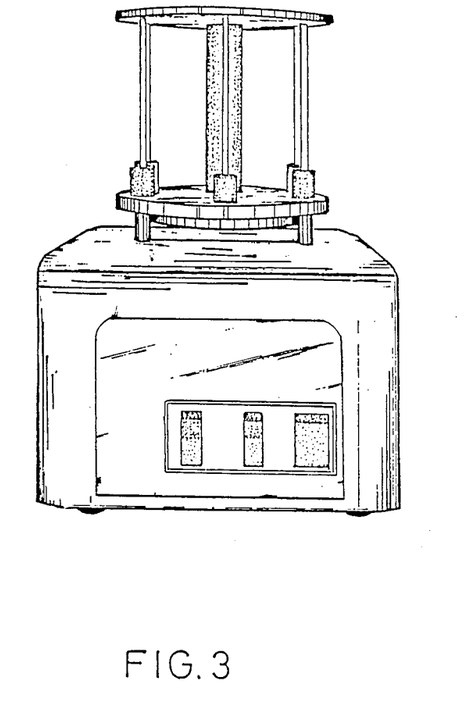
FIG. 3 is a picture of Zetafuge devised by Bull and Brailsford in 1972. Centrifugal force is given by this device to accelerate the sedimentation of erythrocyte.

Many methods have been used to measure ESR. The earliest one is that of Westergren (as shown in FIG. 1), introduced into medicine in 1921, which is still considered the standard method of measuring ESR. With the Westergren method, the anticoagulated blood is filled into a 300 mm long Westergren glass tube to the zero mark located 200 mm from below. The glass tube is set up vertically and left undisturbed for one hour. The distance from the junction of plasma and RBC column to the zero mark after one hour is the ESR desired. The second most popular method is due to Wintrobe and Landsberg (as shown in FIG. 2), introduced in 1935. This method is performed with a 120 mm long tube whose internal diameter is 2.5 mm, the same as that of the Westergren tube. The procedure is similar to that of the Westergren method. In 1972, Bull and Brailsford devised another method called Zeta Sedimentation ratio (ZSR) that is unaffected by anemia and responds in a linear fashion to an increase in plasma fibrinogen or gamma globulin level. The ZSR is measured by using an apparatus named Zetafuge (as shown in FIG. 3) that can produce low-speed centrifugation to speed the sedimentation process. The ZSR technique eliminates some disadvantages of ESR, but unfortunately does not meet with wide acceptance.

Figure 4:
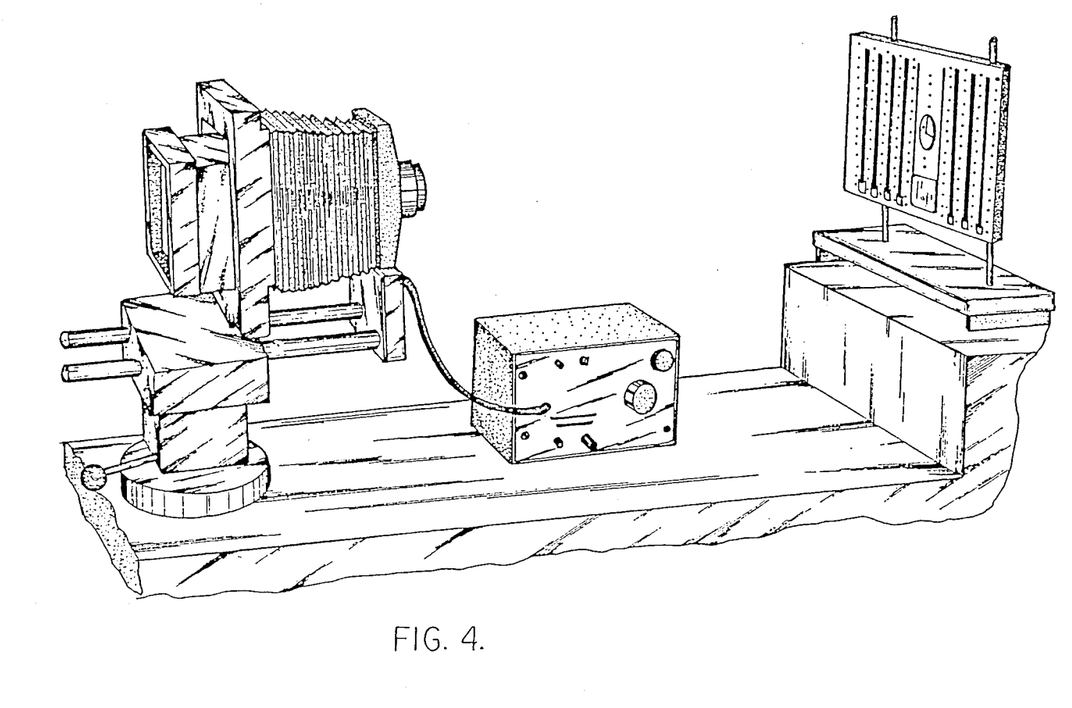
FIG. 4 is a picture of an automated recording device constructed by King et al in 1981. This device can record ESR at only one chosen time by means of a photographic method.

Both the Westergren and Wintrobe-Landsberg methods, or minor modifications of them, are manually operated, and are therefore labor-requiring and subject to technical error. Long term observation of ESR with these methods are also impractical. No automated monitoring, recording device of ESR is available except a photographic method, devised by King et al in 1981 (as shown in FIG. 4), which is still a primitive one piece of in that only one data at one particular time is obtainable. To facilitate detailed recording of ESR, mass screening, statistical analysis, and further study into the obscure nature of erythrocyte sedimentation, the undersigned inventors have developed this automatic monitoring and recording unstrument of erythrocyte sedimentation process.

SUMMARY OF THE INVENTION

The primary object of this invention is to provide clinicians with an automatic monitoring and recording system of erythrocyte sedimentation process. This system makes possible not only detailed recording of the whole course of erythrocyte sedimentation that may give information concerning the disease processes, but also mass sreening of patients with occult illness.

This system makes use of a LED-photodetector pair to detect the light transmittance at the junction of plasma and RBC column. Change in light transmittance at that junction reflects a descent in the RBC column. A microcomputer and step motor are used to feed-back control the position of LED-photodetector pair so that it will always follow the descent of the RBC column.

A fuller understanding of the present invention will become apparent by referring to the following detailed description with reference to the accompanying drawings.

DESCRIPTION OF THE PREFERRED EMBODIMENT

The automatic monitoring and recording system of the present invention is made possible by means of a light source (LED) and photodetector pair. The photodetector on one side of a modified Westergren tube measures the intensity of light emitted from the LED on the other side of the same tube and transmitted through the junction of plasma and RBC column inside the tube. As the RBC column descends because of gravity, the intensity of light transmitted through that junction increases. The increased light transmittance detected by the photodetector is turned into digital data by the A/D converter. The digital data are then fed into the microcomputer to calculate the rapidity of decrease in the RBC column. A controlling program and a step motor are used to feed-back control the position of the LED-photodetector pair so that the beam of light can always pass through the junction of plasma and RBC column during the sedimentation process.

Figure 5:
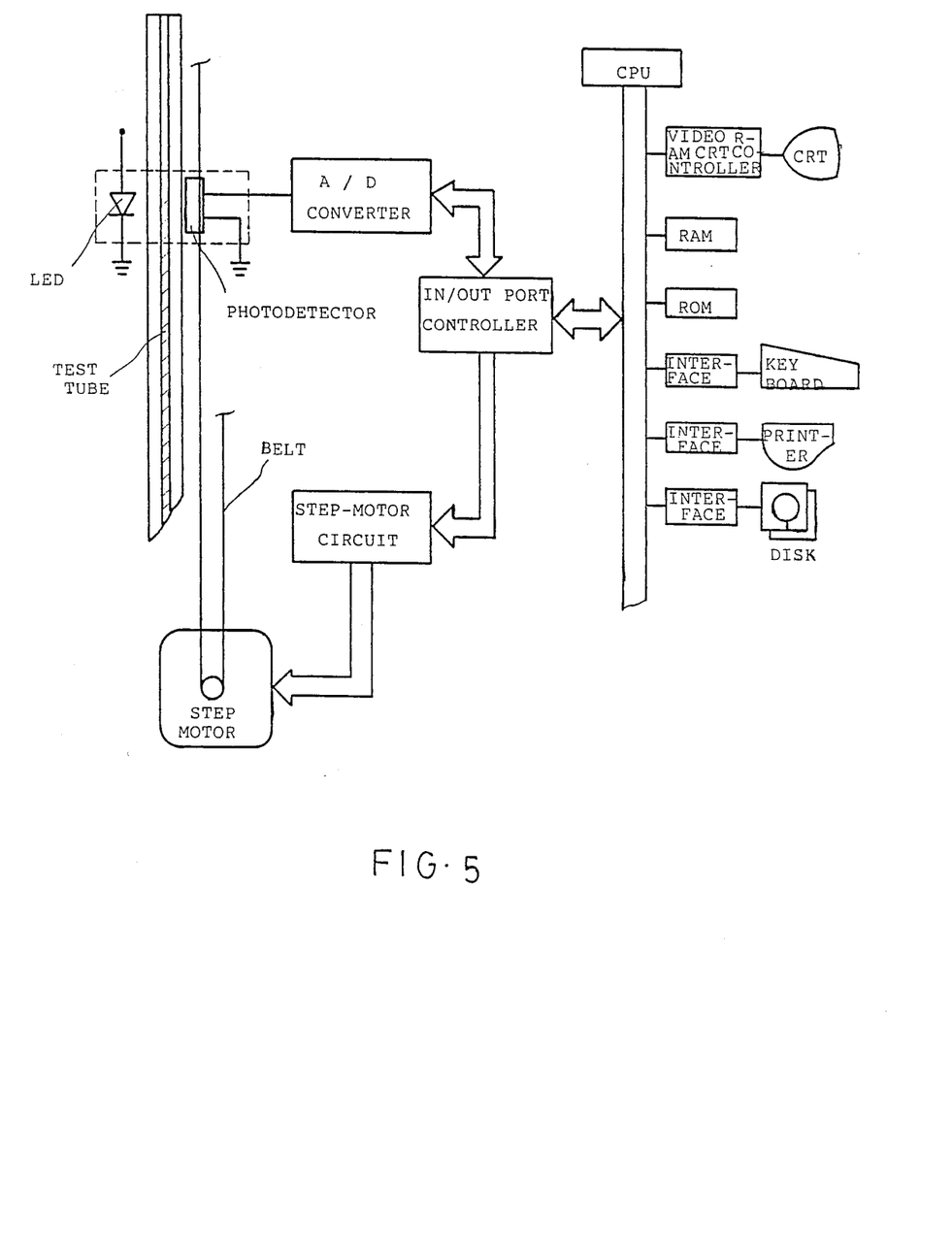
FIG. 5 is a block diagram of the automatic monitoring and recording system of an erythrocyte sedimentation process according to the present invention.

Referring to FIG. 5, the system comprises a microcomputer (20), an I/O port controller (22), an A/D converter (24), a LED (16) and photodetector (17) pair, a step motor (9) and a step motor circuit (26). The LED (16) and photodetector (17) are mounted on either side of an elevator (3) (see FIG. 6) which can slide smoothly along a longitudinal rod (2) encasing the modified Westergren test tube (4). The I/O port controller (22) mediates data transmission. Its functions are twofold: (A) on receiving an instruction from a CPU, the I/O port controller (22) issues a conversion signal to the A/D converter (24) to pick up a voltage value from the photodetector (17). The A/D converter (24) converts the voltage value into a digital signal which is then sent back to CPU for further processing; and (b) transmit the signal from the CPU to the step motor circuit (26) to drive the step motor (7) to rotate a predetermined amount.

Figure 6:
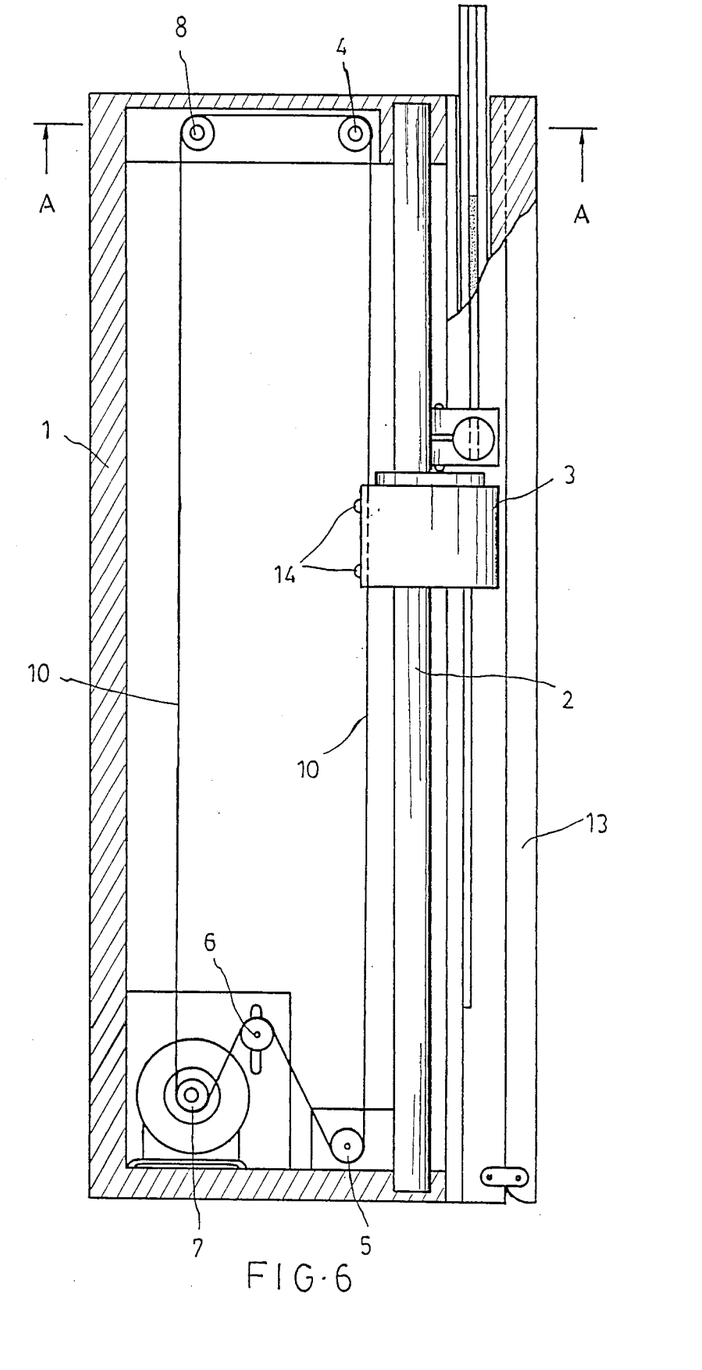
FIG. 6 is a longitudinal sectional view of the supporting frame and the related members according to the present invention.

Referring to FIG. 6, a rubber belt (10) is shown to connect the elevator (3) to the step motor (7) so that the step motor (7) can move the LED (16)-photodetector (17) pair in the elevator (3) upwards or downwards along the longitudinal rod (2). Several rivets (14) fasten the elevator (3) to the rubber belt (10) which goes around the rollers (9), (5), and (8) in the corners and the step motor (7) to complete a circle. To keep the tension of the belt (10) a tensile adjustment roller (6) is placed in the rubber belt path. The whole assembly is encased in a coverframe (1).

Figure 7:
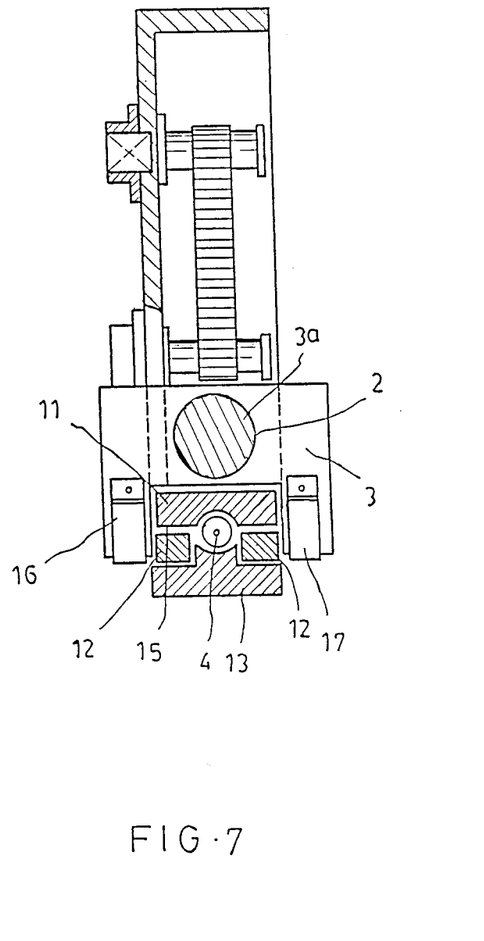
FIG. 7 is a sectional view taken on line A—A' of FIG. 6.

Referring to FIG. 7, the elevator (3) has a shaft hole (3a) for receiving the longitudinal rod (2) and the test tube (4). Between the LED (16) and photodetector (17) in the elevator (3), there are a test tube fixation piece (11), two gap adjustment pieces (12) and one test tube clamping piece (13). The test tube (4) is fixed in place with these pieces. There is a straight gap (15) between the test tube fixation piece (11) and the gap adjustment pieces (12) to permit the light beam from the LED (16) to pass through the test tube (4) and reach the photodetector (17). It is important to align the straight gap (15) with the center axis of the test tube (4) all the way along the elevator (3) as it moves up and down along the longitudinal rod (2) so that the light from LED (16) can always pass through the blood column without missing a single data point.

Figure 8:
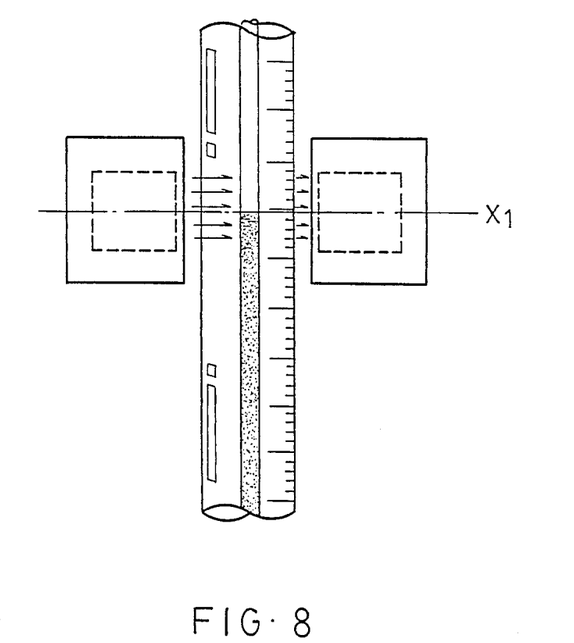
FIGS. 8 and 9 are diagrams of the principle of automatic monitoring and recording of erythrocyte sedimentation employed in the present invention.
Figure 9:
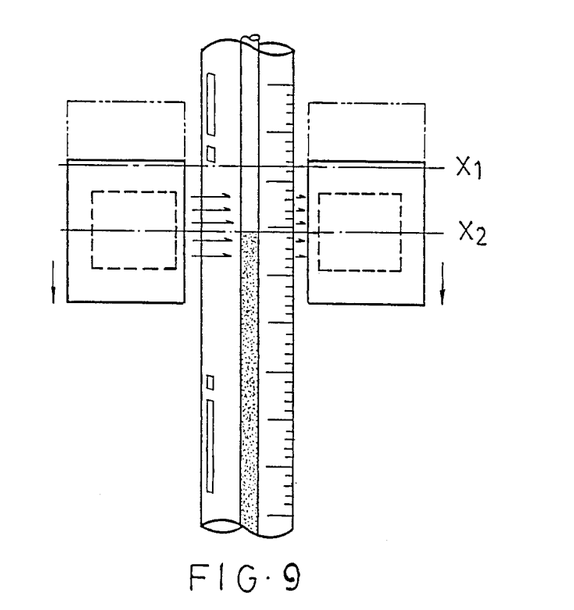

Referring to FIGS. 8 and 9, it can clearly be seen that when the test tube (4) is placed vertically for a while, the blood inside the tube will gradually separate into two distinct compartments, i.e., the upper semitransparent part composed of plasma, and the lower opaque part composed of blood cells, mainly RBCs. As time goes on, the RBCs will descend because of cell aggregation and gravity. The intensity of light passing through the junction of plasma and RBC column will also be increased gradually due to the increased amount of semitransparent plasma. Upon detecting the increased light transmittance, the photodetector notifies the microcomputer which then sends a signal to the A/D converter to drive the step motor (7) and the elevator (3) that harbors the LED (16) and photodetector (17) pair to move downward from $X_1$ to $X_2$ accordingly. The result is the repositioning of the LED-photodetector pair exactly at the junction of plasma and RBC column. This iterative process of downward movement and re-positioning of the LED-photodetector pair continues on and on until the required duration of monitoring is finally met.

Figure 10:
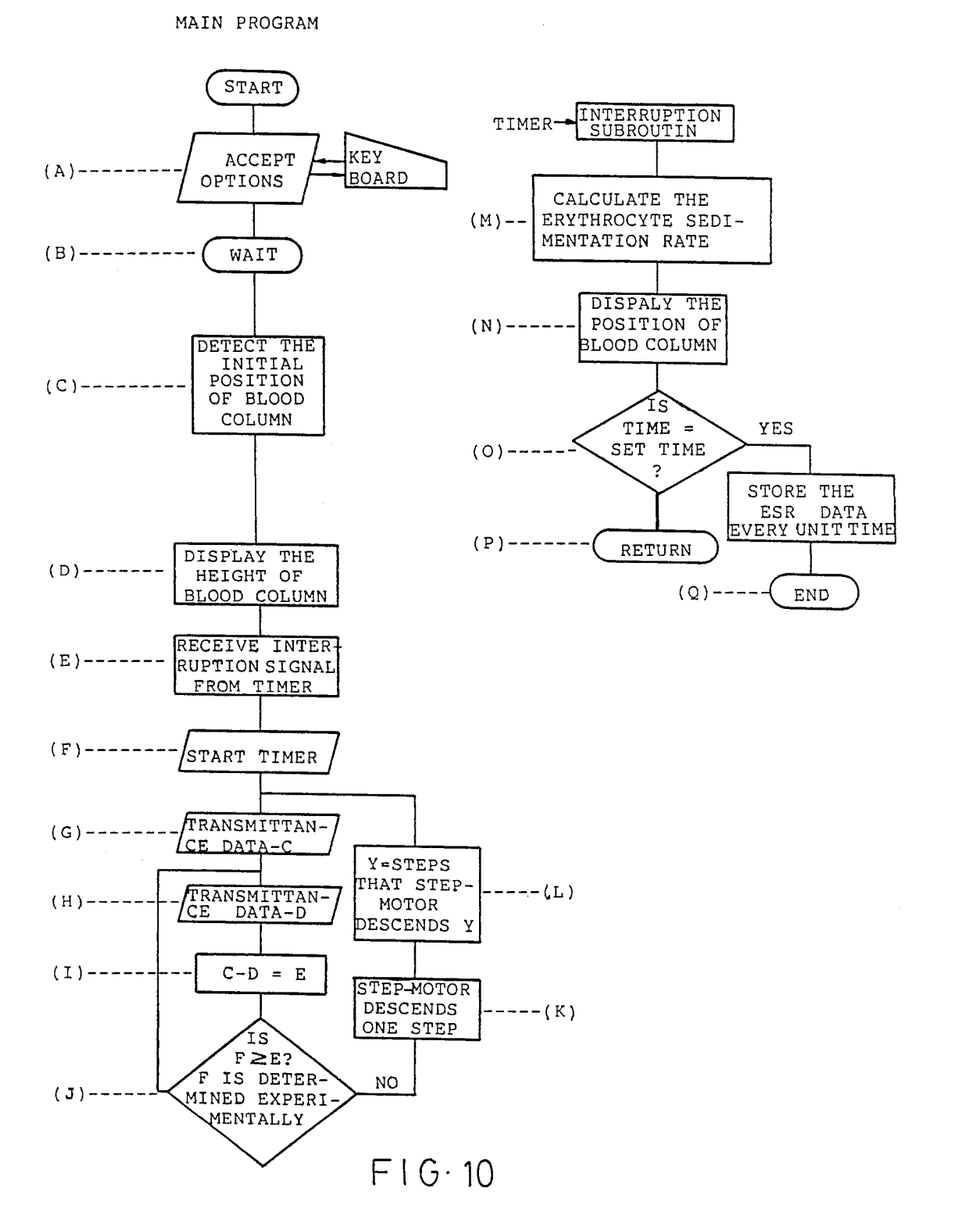
FIG. 10 is a flow-chart of the operation according to the present invention.
Figure 11:
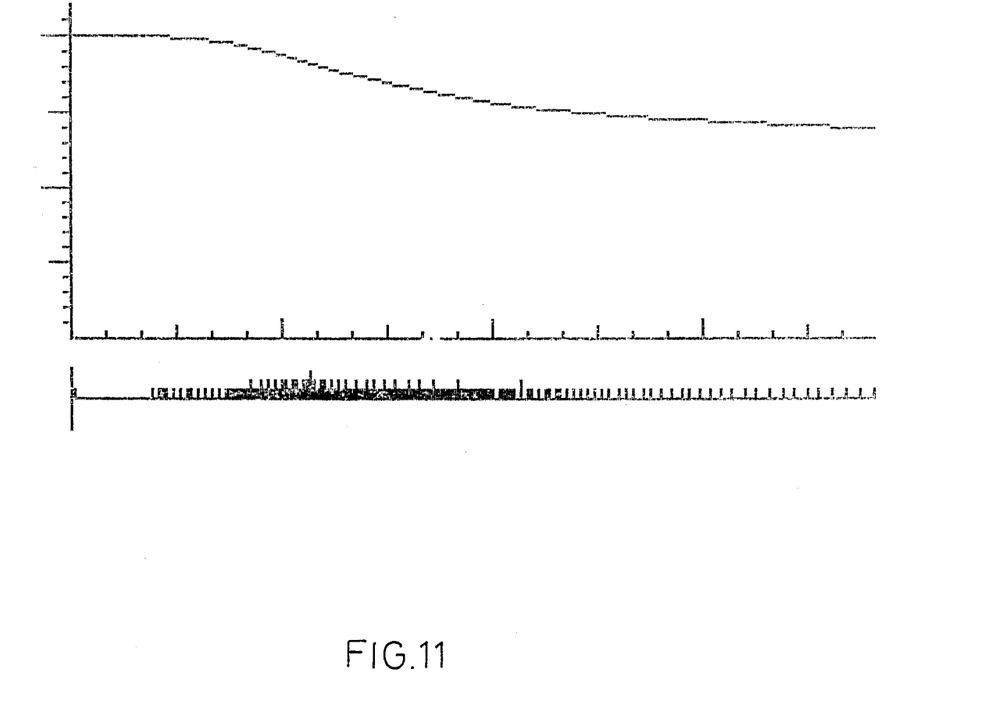
FIGS. 11, 12 and 13 are print-outs of erythrocyte sedimentation curves and their velocity profiles.
Figure 12:
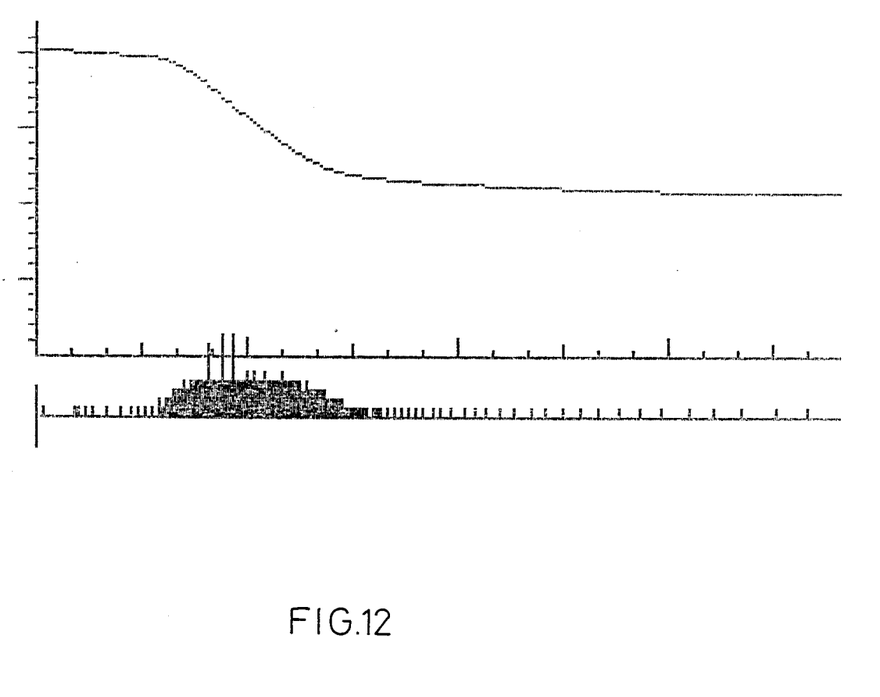
Figure 13:
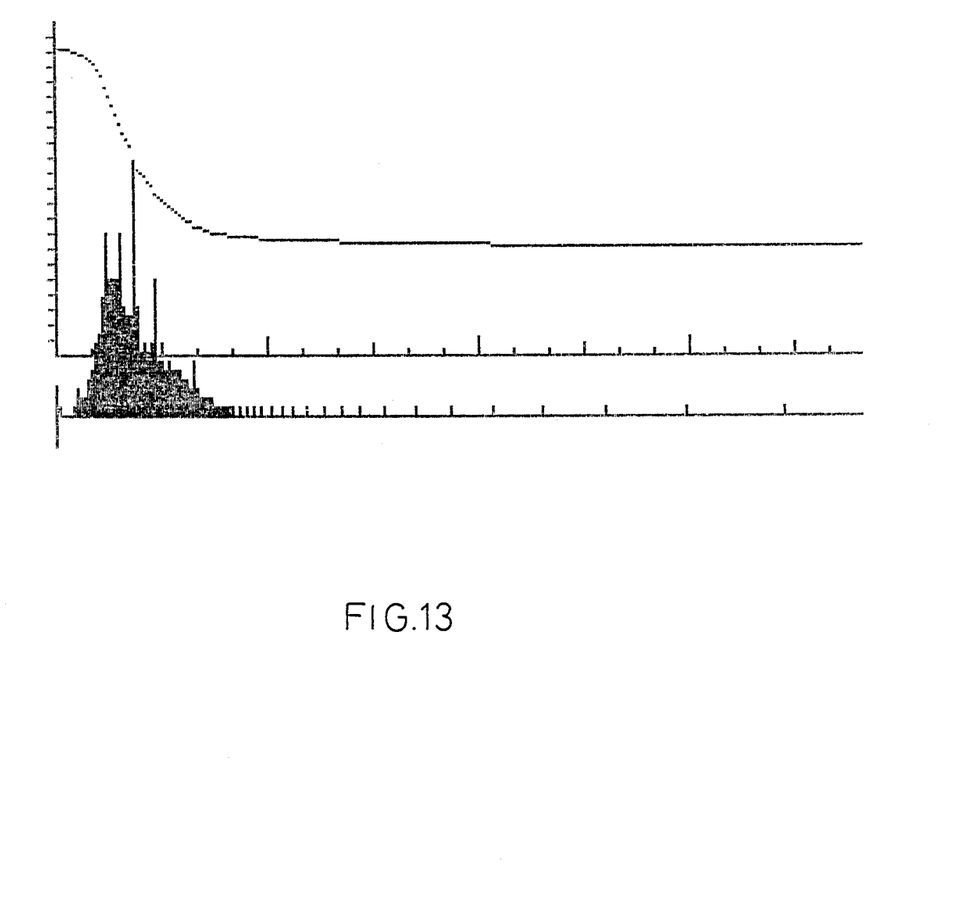

Referring to FIG. 10, a flow-chart of the present invention is shown. The software consists of one main program and an interruption subroutine. The flowchart of ESR software shows the test procedures and the interrelations between routines and files. Briefly speaking, the test procedures are as follows:

(I) Use the photodetector (17) to measure the light transmittance at the junction of plasma and RBC column.

(II) Use the microcomputer (20) to calculate the rate of descent of RBC column.

(III) In accordance with the calculated rate of descent of RBC column, the step motor circuit (26) will drive the step motor (7) a given amount to move the LED-photodetector to a new position of the junction of plasma-RBC column.

(IV) A timer will send out an interruption signal periodically to interrupt the CPU, and let it jump to the interruption subroutine to execute the calculation of the rate of descent of RBC column.

The flow-chart is described in detail as follows:

(A) Use a key-board to key-in requested data such as the name of the patient, chart number, clinical diagnosis, specific drugs used that will affect ESR, date and time of the test, required measurement time interval, etc.

(B) Wait for the insertion of the test tube containing blood into the instrument, and the depression of the RETURN key for initiation; then, the manual part of the blood test is completed.

(C) The LED-photodetector pair will automatically detect the initial position of the junction of plasma and RBC column.

(D) Display on the monitor screen the height of that junction.

(E) Set up the interruption function.

(F) Start the timer.

(G) The photodetector measures the initial light transmittance at the junction of plasma and RBC column. Assign the value as C.

(H) The photodetector measures again the light transmittance of the tested blood in a later moment. Assign the value as D.

(I) Subtract D from C, and let the result be E.

(J) If E is less than an experimentally determined value F, then go to (H) to repeat the same process of photodetection.

(K) If E is larger than F, then the step motor will drive the LED-photodetector pair one step downward.

(L) Accumulate the steps that the step motor has moved.

(M) Calculate the erythrocyte sedimentation rate (ESR) at the time of interruption.

(N) Display the position of the junction of plasma and RBC column on the monitor screen. The calculated ESR is also shown on the screen.

(O) If the desired duration of the blood test is not met yet, then return to the main program.

(P) If the desired duration of the blood test is met, then store the data of erythrocyte sedimentation in every unit time in the diskette.

(Q) End.

Although this invention has been described in its preferred form with a certain degree of particularity for the purpose of enabling a person of ordinary skill to make and use the invention, it should be asserted that any change, modification and arrangement in the parts must be considered to be without departing from the spirit and scope of the invention as hereinafter claimed.

We claim:

1. An automatic monitoring and recording system for erythrocyte sedimentation of plasma, comprising:
   light source means for emitting light;
   photodetector means coupled to receive the light emitted from said light source means, for detecting the change in the intensity of light emitted from said light source means and transmitted through the junction of plasma and red blood cell column and outputting a signal; and
   a microcomputer, connected to receive the signal from said photodetector means, for calculating the erythrocyte sedimentation rate.

2. An automatic monitoring and recording system for erythrocyte sedimentation as claimed in claim 1, further comprising a control system, including a step motor for driving said control system, for making said light source means and photodetector means always aim at the junction of plasma and red blood cell column.

3. A computerized automatic monitoring and recording system for determining erythrocyte sedimentation rate, comprising:
   a light emitted diode (LED)-photodetector pair, said photodetector receiving light emitted from said LED and outputting an analog signal;
   containing means, placed between said LED-photodetector pair, having plasma and red blood cells therein, said LED-photodetector pair determining the junction of the plasma and red blood cells;
   A/D converter means, connected to said photodetector for receiving and converting the analog signals from said photodetector to digital signals;
   input/output means, connected to said A/D converter means, for receiving the digital signals from said A/D converter means and outputting signals;
   a step motor circuit, connected to said input/output means, for receiving signals from sid input/output means;
   a step motor, connected to said step motor circuit, for moving said containing means between said LED-photodetector pair for determining the junction of plasma and red blood cells; and
   a microcomputer, coupled to said input/output means, for providing data regarding the plasma and red blood cells in said containing means, for controlling said input/output means for controlling the movement of said LED-photodetector pair, for determining the junction of plasma and red blood cells from the digital signals from said photodetector, and for storing, printing and displaying the results.

4. A computerized automatic monitoring and recording system as set forth in claim 3, further comprising an elevator, coupled between said LED-photodetector pair, encasing said containing means and sliding along said containing means by means of said servomotor.

5. A computerized automatic monitoring and recording method for determining erythrocyte sedimentation, said method comprising the steps of:
   (a) inputting data to a microcomputer regarding blood in a test tube to be tested;
   (b) detecting the initial position of the junction of plasma and red blood cells in the test tube by a LED-photodetector pair;
   (c) displaying the height of the junction of plasma and red blood cells in the test tube;
   (d) measuring the initial light transmittance at the junction of plasma and red blood cells;
   (e) measuring, a predetermined time later, the light transmittance at the junction of plasma and red blood cells;
   (f) determining the difference between the results obtained in said steps (d) and (e);
   (g) repeating said steps (e) and (f) if the result in said step (f) is less than an experimentally obtained value;
   (h) driving the LED-photodetector pair one step downward if the result in said step (f) is greater than the experimentally obtained value;
   (i) calculating the erythrocyte sedimentation rate;
   (j) displaying the position of the junction of plasma and red blood cells and the calculated erythrocyte sedimentation rate;
   (k) continuing calculating the erythrocyte sedimentation rate for a predetermined period of time; and
   (l) storing the erythrocyte sedimentation rate for every unit of time.

* * * * *